(12) United States Patent
Meyers et al.

(10) Patent No.: US 7,896,298 B2
(45) Date of Patent: Mar. 1, 2011

(54) INTRAVENOUS SUPPORT APPARATUS

(75) Inventors: Daniel Seth Meyers, Roxboro (CA); Cristian Boar, Montreal (CA); Ming Xu, Saint-Laurent (CA)

(73) Assignee: AMG Medical Inc., Montreal, Quebec (CA)

( * ) Notice: Subject to any disclaimer, the term of this patent is extended or adjusted under 35 U.S.C. 154(b) by 244 days.

(21) Appl. No.: 12/171,468

(22) Filed: Jul. 11, 2008

(65) Prior Publication Data
US 2010/0006718 A1 Jan. 14, 2010

(51) Int. Cl.
*A47K 1/04* (2006.01)
(52) U.S. Cl. .................................. 248/125.8; 248/124.1
(58) Field of Classification Search ............... 248/125.8, 248/188–188.91
See application file for complete search history.

(56) References Cited

U.S. PATENT DOCUMENTS

| | | | |
|---|---|---|---|
| 1,261,755 A | | 4/1918 | Beyle |
| 3,754,874 A | * | 8/1973 | Anderson ...................... 428/653 |
| 3,863,876 A | | 2/1975 | Finkelstein et al. |
| 4,225,104 A | | 9/1980 | Larson |
| 4,332,378 A | | 6/1982 | Pryor |
| 4,520,981 A | * | 6/1985 | Harrigan ...................... 248/413 |
| 4,546,774 A | | 10/1985 | Haught |
| 4,653,710 A | * | 3/1987 | Dickison ...................... 248/188.7 |
| 4,666,111 A | | 5/1987 | Schuler |
| 4,744,536 A | * | 5/1988 | Bancalari ...................... 248/125.8 |
| 4,807,837 A | * | 2/1989 | Gawlik et al. .............. 248/125.8 |
| 4,821,986 A | * | 4/1989 | White ........................ 248/188.7 |
| 4,886,237 A | | 12/1989 | Dennis |
| 4,905,944 A | * | 3/1990 | Jost et al. .................... 248/125.8 |
| 4,966,340 A | | 10/1990 | Hunter |
| 5,024,665 A | * | 6/1991 | Kaufman ...................... 604/179 |
| 5,083,807 A | | 1/1992 | Bobb et al. |
| 5,124,857 A | | 6/1992 | Pitz |
| 5,135,125 A | | 8/1992 | Andel et al. |
| 5,174,533 A | | 12/1992 | Pryor et al. |
| 5,319,816 A | | 6/1994 | Ruehl |
| 5,458,305 A | * | 10/1995 | Woodward .................... 248/121 |
| D372,533 S | | 8/1996 | Davis |

(Continued)

FOREIGN PATENT DOCUMENTS

EP 0 051 732 A1 5/1982

(Continued)

OTHER PUBLICATIONS

European Patent Office Search Report dated Dec. 30, 2008 on Applicants' corresponding European Patent Application No. 08254228.9-1526.

*Primary Examiner* — Terrell Mckinnon
*Assistant Examiner* — Erin Smith
(74) *Attorney, Agent, or Firm* — Ogilvy Renault LLP

(57) ABSTRACT

An intravenous support apparatus comprises a pole, means attachable to the pole for hanging an intravenous liquid supply on the pole, and a base including a plurality of disconnectable legs having respective inner ends joined one with another, the joined inner ends forming a central body of the base to define a central passage extending vertically through the base, the central passage receiving a bottom end of the pole for supporting the pole in a upright position, each leg including a first material containing a core element of a second material which is heavier than the first material.

16 Claims, 6 Drawing Sheets

U.S. PATENT DOCUMENTS

| | | |
|---|---|---|
| 5,551,105 A | 9/1996 | Short |
| 5,576,722 A | 11/1996 | Bustillos |
| D377,092 S | 12/1996 | Ebert |
| 5,704,577 A | 1/1998 | Gordon |
| 5,772,162 A * | 6/1998 | Lin .............................. 248/121 |
| 5,980,658 A * | 11/1999 | Sukonnik et al. ............. 148/529 |
| 6,079,678 A | 6/2000 | Schott et al. |
| D436,167 S | 1/2001 | Ebert |
| 6,179,260 B1 | 1/2001 | Ohanian |
| D457,239 S | 5/2002 | Kunik |
| 6,808,153 B1 * | 10/2004 | Kelley ....................... 248/441.1 |
| 6,969,031 B2 | 11/2005 | Ugent et al. |
| 6,983,915 B2 | 1/2006 | Adelman |
| 7,156,354 B2 * | 1/2007 | Shepherd et al. ............. 248/407 |
| 7,159,828 B1 * | 1/2007 | Yau et al. ................... 248/125.8 |
| 7,200,935 B2 * | 4/2007 | Davenport ...................... 29/895 |
| 7,281,691 B2 | 10/2007 | Adelman |
| 7,458,439 B2 * | 12/2008 | Catton et al. .................. 180/334 |
| 7,481,254 B2 * | 1/2009 | Welsh et al. ................ 144/286.1 |
| 7,775,377 B2 * | 8/2010 | Abney ......................... 211/13.1 |
| 2001/0019095 A1 * | 9/2001 | Valiulis ...................... 248/188.7 |
| 2005/0139736 A1 * | 6/2005 | Breda et al. .................. 248/129 |
| 2007/0221796 A1 * | 9/2007 | Silverman et al. ............ 248/161 |

FOREIGN PATENT DOCUMENTS

EP           1 212 963 A1     6/2002

* cited by examiner

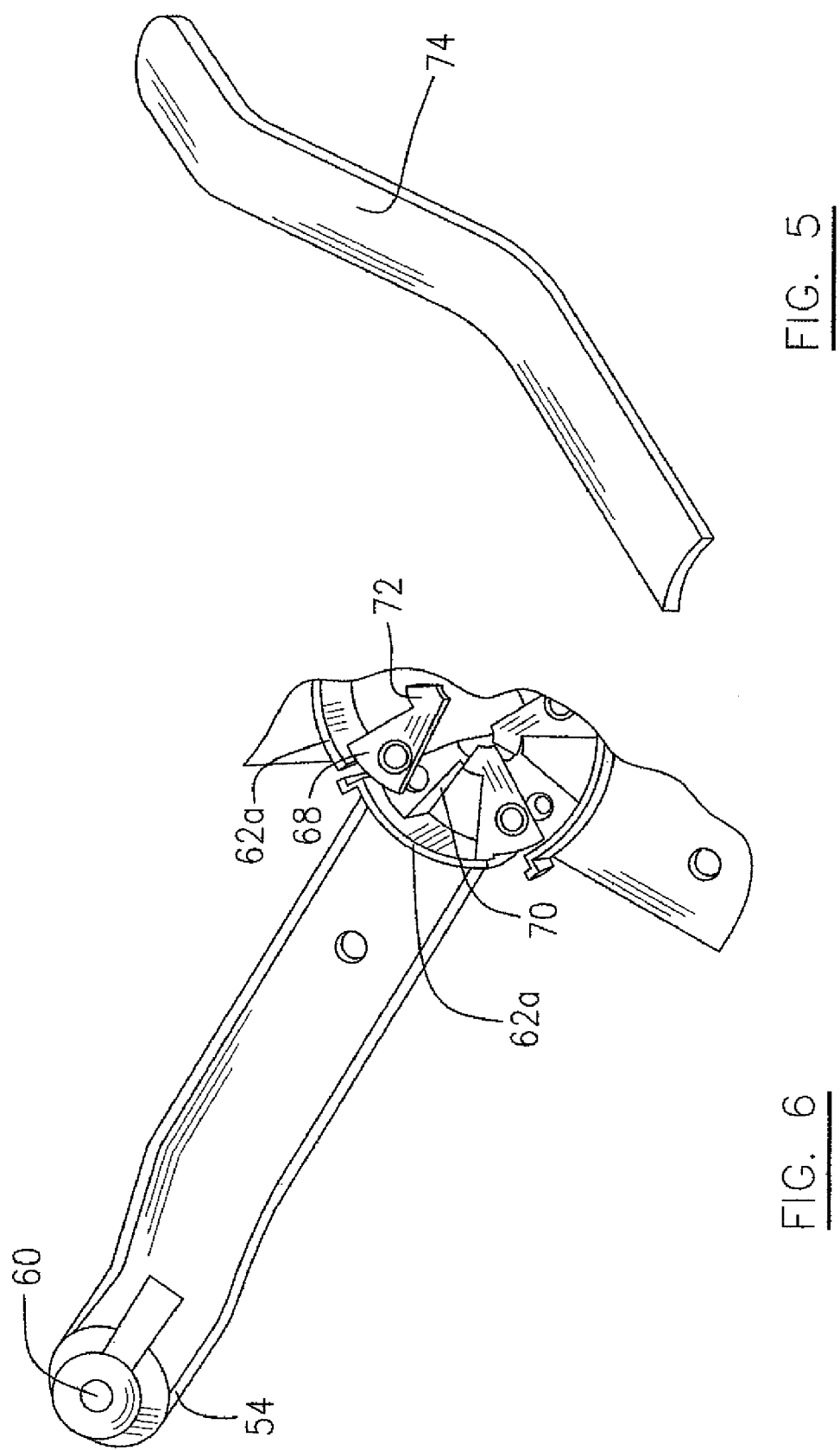

INTRAVENOUS SUPPORT APPARATUS

FIELD OF THE INVENTION

The present invention relates generally to the field of medical equipment and, more particularly, to an intravenous support apparatus to hang an intravenous liquid supply in order to enable gravity flowing of the intravenous liquids to a patient.

BACKGROUND OF THE INVENTION

Intravenous support apparatuses which are usually referred to as I.V. stands or I.V. poles, are conventionally constructed having a tall slender upright post or pole mounted onto a relatively small-sized base, sometimes with small wheels. The post or pole is fitted with a hanger at the top from which the bottles or pouches of intravenous liquids are hung. Optionally, as I.V. pump may be supported on the post or pole and connected to the bottles or pouches to pump liquids. For convenience of use, I.V. stands are sometimes configured having the post or pole in a telescoping configuration in which the sections of the post or pole have a diameter smaller one than another from a bottom section to a top section, in order to allow adjustment of the height level of the bottles or pouches of the intravenous liquids for controlling the gravity flowing of the liquids and for convenience of access.

Also for convenience of use, the base of stands are usually relatively small. However, even under the regular load of the weight of the bottles or plastic pouches containing liquids, which are hung on the top of the post or pole, the I.V. stands are relatively unstable and can be rather easily knocked over. Therefore it is not unusual for the conventional I.V. stands to have additional support for attaching either the pole or the base of an I.V. stand to a bed or wheelchair, etc. on which a patient rests while receiving intravenous injection. Furthermore, it is not unusual for doctors and nurses to hang additional loads such as medical instruments, devices or other articles on the post or pole of an I.V. stand. Therefore, the stability of such stands and the rigidity and strength of the post or pole of I.V. stands are particularly important. Another disadvantage of conventional I.V. stands lies in that a disassembled I.V. stand is usually packed in a relatively large box due to the relatively large sizes of the components, particularly the base unit. Therefore, it is also desirable to have an I.V. stand assembly which can be disassembled into a kit package having relatively small dimensions for shipping and storage.

SUMMARY OF THE INVENTION

In accordance with one aspect of the present invention, an intravenous support apparatus comprises a pole; means removably attached to the pole for hanging an intravenous liquid supply on the pole; and a base including a plurality of disconnectable legs having respective inner ends joined one with another, the joined inner ends forming a central body of the base to define a central passage extending vertically through the base, the central passage receiving a bottom end of the pole for supporting the pole in a upright position, each leg including a first material containing a core element of a second material which is heavier than the first material.

In accordance with another aspect of the present invention, there is provided a kit for an assembly of an intravenous support apparatus which comprises a first section of a pole; a hollow second section of the pole for receiving the first section in a telescoping configuration; a hollow third section of the pole; a joint element for joining the second and third sections together; means attachable to the pole for hanging an intravenous liquid supply on the pole; and a plurality of legs to be joined to form a base for supporting the pole in an upright position, the legs having respective inner ends adapted for joining one with another to form a central body defining a central passage for receiving a bottom end of the pole, each leg including a first material which contains a core element of a second material heavier than the first material.

BRIEF DESCRIPTION OF THE DRAWINGS

Further features and advantages of the present invention will become apparent from the following detailed description, taken in combination with the appended drawings, in which:

FIG. 4 is a cross-sectional view of the leg of FIG. 3 taken along 4-4, showing the two-piece configuration of the leg;

FIG. 5 is a perspective view of a core element of the leg of FIG. 4;

FIG. 6 is a partial perspective bottom view of three legs of the intravenous stand of FIG. 1 in an assembly procedure, showing the side connectors of adjacent legs for connection to each other;

It will be noted that throughout the appended drawings, like features are identified by like reference numerals.

DETAILED DESCRIPTION OF THE PREFERRED EMBODIMENT

Figure 1:
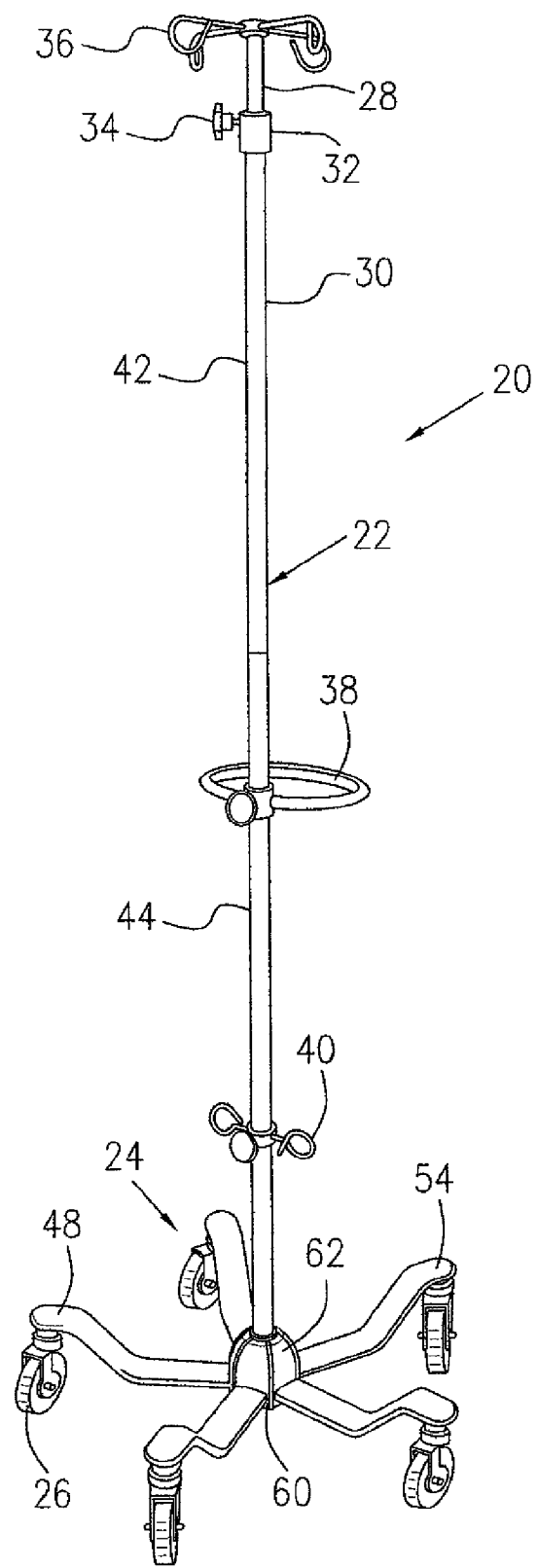
FIG. 1 is a perspective view of an intravenous stand according to one embodiment of the present invention.

In FIG. 1, an intravenous support apparatus generally referred to as an intravenous (I.V.) stand 20 includes a pole 22 in a substantially upright position, inserted into and supported by a base assembly 24 which preferably has a plurality of small wheels, such as wheel assemblies 26 for convenience of transportation.

Figure 2:
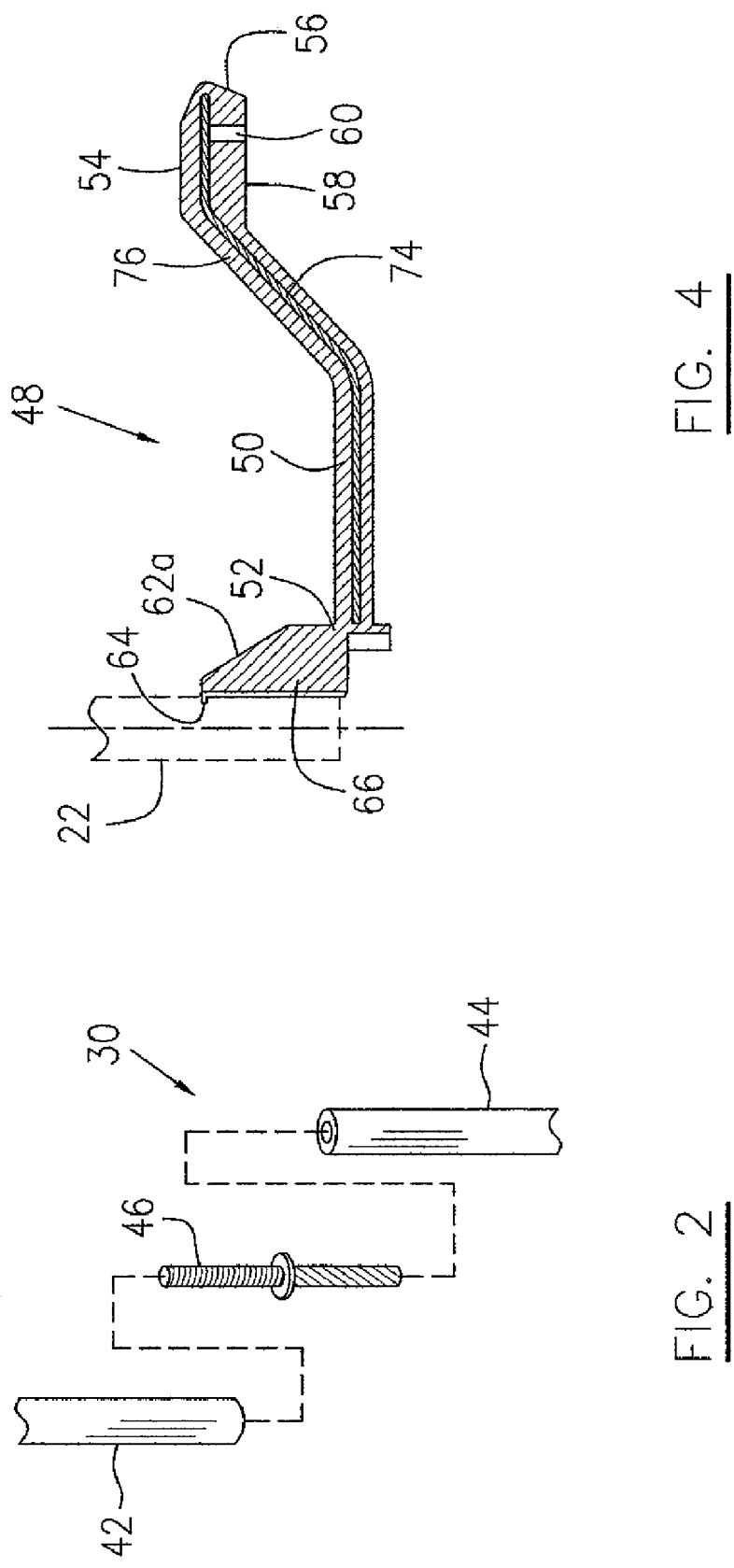
FIG. 2 is an exploded, perspective partial view of a pole of the intravenous stand of FIG. 1, showing a joint member for joining upper and lower parts of a bottom section of the pole.
Figure 3:
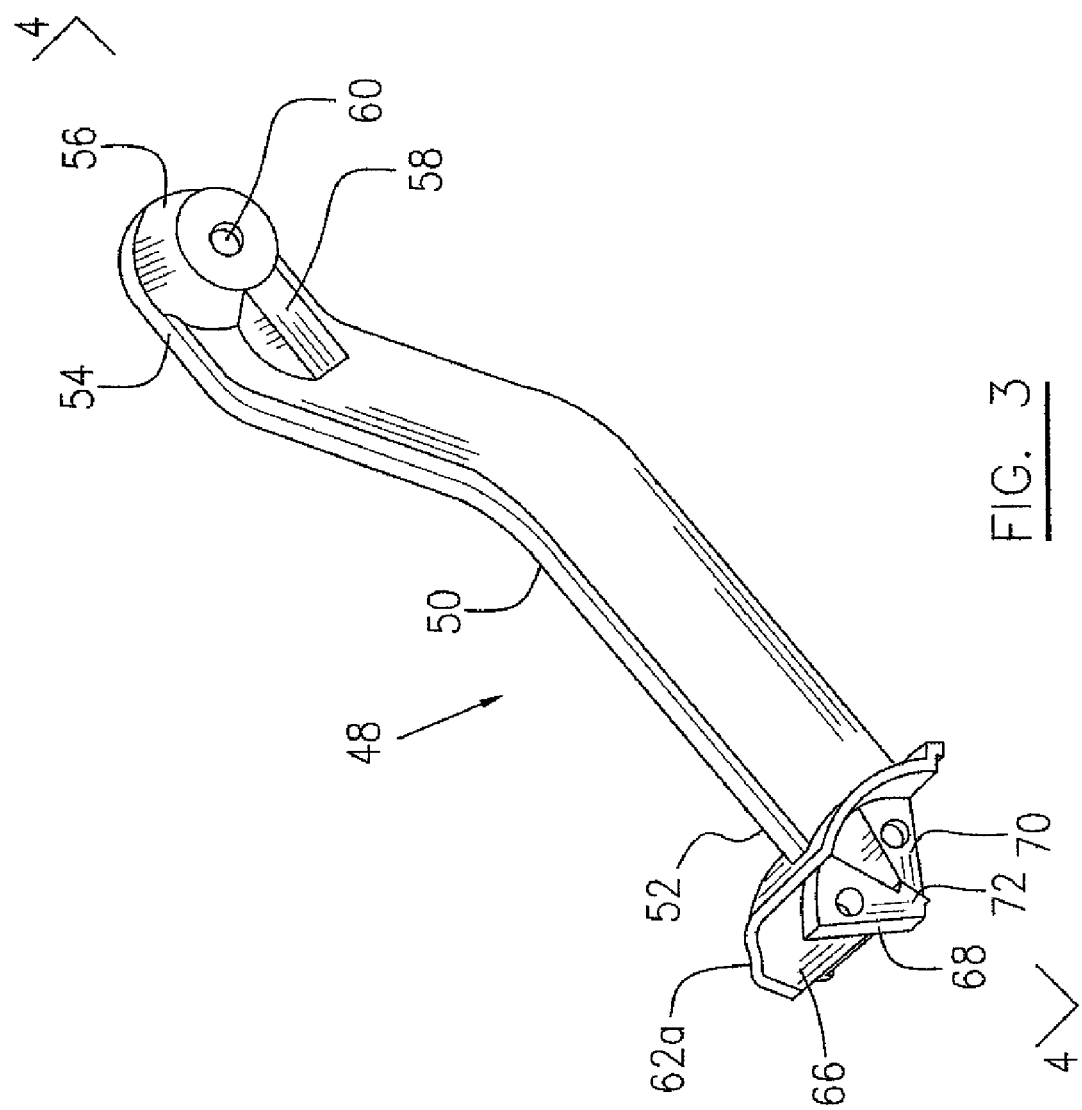
FIG. 3 is a perspective bottom view of a disconnectable leg which is part of a base of the intravenous stand of FIG. 1.

Referring to FIGS. 1 and 2, the pole 22, according to one embodiment of the present invention, may include a top section 28 and a bottom section 30 which is in a hollow configuration, such as of a steel tube. The top section 28 may also be made of a steel tube but has another diameter smaller than the inner diameter of the bottom section 30 so as to allow the top section 28 to be inserted into the bottom section 30 to form a telescoping configuration. Therefore, the top section 28 can be extended upwardly from or be retracted downwardly into the bottom section 30. A lock device may be provided to lock the top section 28 in a selected position with respect to the bottom section 30. The lock device for example may include a sleeve member 32 frictionally affixed on a top end of the bottom section 30 for receiving a locking screw 34 transversely extending through the sleeve member 32 to press against the top section 28 as it extends through the sleeve member 32.

Means are also provided for hanging intravenous bottles or pouches of intravenous liquids on the pole 22. For example, hooks 36 are removably attached to a top end of the top section 28 as shown in FIG. 1. Optionally, other accessories such as a patient handle 38 and additional hooks 40 may be attached to the pole, preferably on the bottom section 30 in a height adjustable manner, which, for example, may be used to support an I.V. pump if needed.

In consideration of convenience for packaging, the pole 22, particularly the bottom section 30 thereof, may include separable upper and lower parts 42, 44, which are both made from, for example, a same steel tube, therefore having substantially equal outer diameters and having substantially equal inner diameters greater than the outer diameter of the top section 28. As more clearly illustrated in FIG. 2, the upper part 42 and lower part 44 are joined end to end to form the bottom section 30 of the pole 20. A joint member 46 may be used to join the upper and lower parts 42, 44 together. The joint member 46, for example, includes a threaded bolt with a middle shoulder (not indicated). The shoulder preferably has an outer diameter substantially equal to the outer diameter of the upper and lower parts 42, 44 and the threading extends along the entire length of the bolt. The threads defined in the respective upper section and lower section of the bolt, which are separated by the middle shoulder, may have opposite rotational directions for convenience of engagement with complimentary inner threads defined in the respective upper and lower parts 42, 44 of the bottom section 30. In such a configuration, the pole 20 can be conveniently disassembled into three tubular sections which may have roughly similar lengths for packaging, while a height adjustment can be easily achieved with the telescoping configuration between the top section 28 and the upper part 42 of the bottom section 30. In a conventional multiple telescoping configuration however, three or more sections of the pole are all connected in telescoping configurations and the diameter of the respective telescoping sections of the pole from the bottom to the top is progressively smaller one than another, which provides height adjustability but compromises the strength and rigidity of the pole and thus the load bearing capacity of the I.V. stand. The embodiment of this invention however maintains one telescoping configuration for convenience of height adjustment of the pole while providing a more secure but disconnectable joining structure between the upper and lower parts 42, 44 of the bottom section 30 of the pole, which advantageously and significantly increases the strength and rigidity of the pole 22 and thereby increases the lead bearing capacity of the intravenous stand 20.

In FIG. 1 and 3-8, the base assembly 24 of the I.V. stand 20 according to one embodiment includes a plurality of disconnectable legs 48 (five legs shown in this embodiment). Each leg 48 is configured, for example with a substantially flat body 50 with an inner end 52 and an outer end 54. The outer end 54 may have a boss 56 defining a bottom surface 58 and a hole 60 which extends inwardly and upwardly from the bottom surface 58 for receiving a shaft (not shown) of the small wheel assembly 26 when the wheel assembly 26 is attached to the outer end 54 of the leg 48, abutting the bottom surface 58.

The inner ends 52 of the respective legs 48 join one to another to form a central body 62 (see FIG. 1) of the base assembly 24 and to define a central passage 64 (see FIG. 7) extending substantially vertically through the base assembly 24. The central passage 64 receives a bottom end of the pole 22, for example the bottom end of the lower part 44 of the bottom section 30 of the pole, for supporting the pole 22 in an upright position as shown in FIG. 1. The bottom end of the pole 22 is secured within the central passage 64 of the central body 62 using a bottom plate 67 (see FIG. 8) attached to the bottom side of the central body 62 and a screw fastener (not shown) inserted through a central passage 64 of the plate 67. The screw fastener is securely engaged with the inner thread of the bottom end of the pole 22 (the bottom end of the lower part 44 of the bottom section 30 of the pole 22 in this embodiment). The substantially flat body 50 of the respective legs 48 may be bent such that the central body 62 formed with the respective inner ends 52 of the legs 48 is positioned at a level which is lower than a height level of the outer ends 54 of the legs 48 when the I.V. stand 20 is standing upright on the ground or floor. Therefore, when the outer ends 54 of the legs 48 are supported by the respective small wheel assemblies 26 at a relatively higher level with respect to the ground, the central body being in a relatively lower position, advantageously increases the stability of the I.V. stand 20 when the pole 20 is loaded.

Each of the inner ends 52 of the respective legs 48, is integrated with a sectorial fraction 62a of the central body 62 of the base assembly 24 (1/5 of the central body 62 in this embodiment). The sectorial fraction 62a which may be configured in a shell configuration, and projects upwardly from the inner end 52 of the leg 48, thereby forming an upwardly projecting profile of the central body 62 when the five legs 48 are assembled together to form the base assembly 24. The upwardly projecting profile of the central body 62 provides a vertical dimension for more effectively securing the bottom end of the pole 22. The shell configuration of the sectorial fraction 62a of each leg 48 may include a central wall 66 to increase the rigidity of the hollow configuration of the central body 60 formed by the individual shell configurations of the sectorial fractions 62a of the legs 48.

Figure 7:
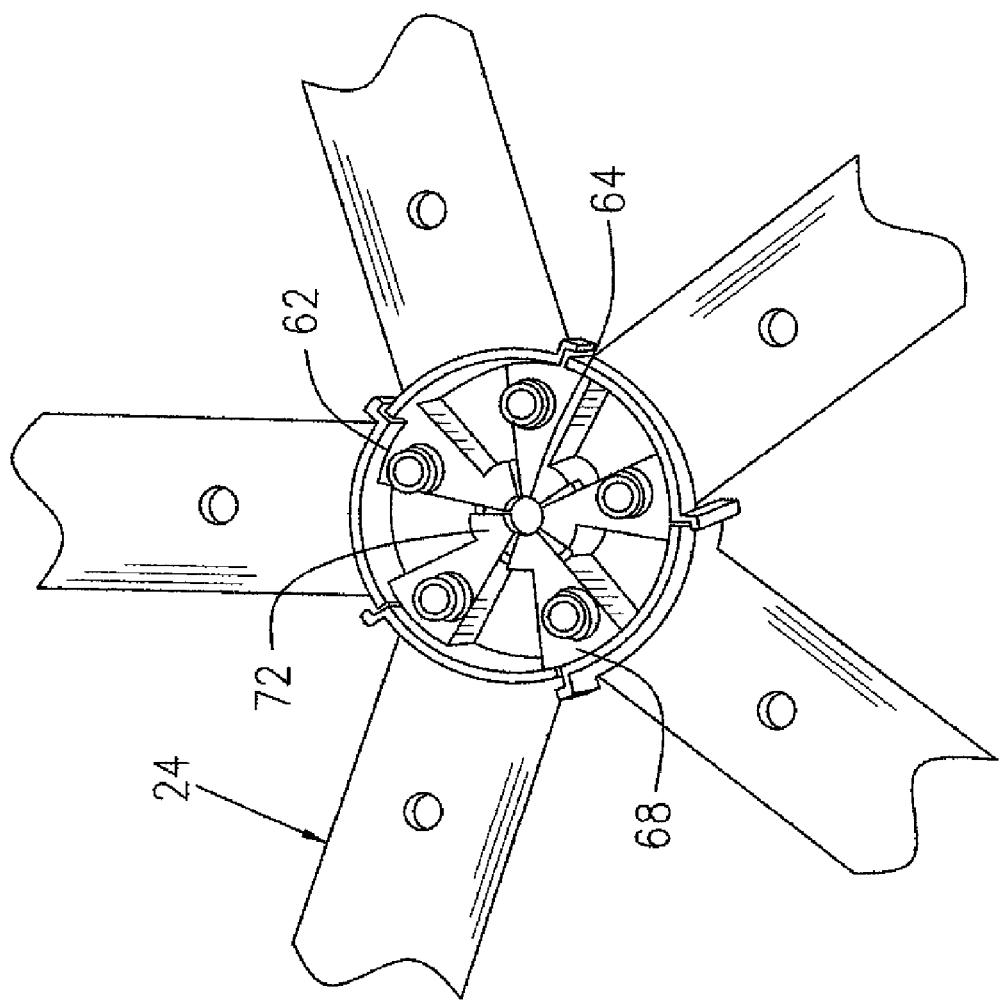
FIG. 7 is perspective bottom view of an assembled base of the intravenous stand of FIG. 1, showing the legs connected one to another.

The inner end 52 of each leg 48 may be incorporated with a pair of side connectors 68 and 70 which are adapted to be positioned adjacent one another and to be connected when the respective legs 48 are assembled together, thereby joining the inner ends 52 of the legs 48 and securing the respective sectorial fractions 62a in position to form the complete central body 62. The respective side connectors 68 and 70 of each leg 48 are configured substantially in a sectorial configuration and are affixed to the inner end 52 of the leg 48 in locations offset one to another both in circumference and in height with respect to the shell configuration of the sectorial fraction 62a. For example, side connector 68 projects circumferentially out of the shell configuration of the sectorial fraction 62a and is adapted to be received within the adjacent shell configuration of sectorial fraction 62a when the legs 48 are assembled together (see FIG. 6). Side connector 70, however, is substantially located within the shell configuration of sectorial fraction 62a at the other side thereof and at a relatively higher location with respect to the ground when the I.V. stand is positioned upright on the ground or floor, so as to match a corresponding side connector 68 of an adjacent leg 48 which extends into a space below the side connector 70 when the adjacent leg 48 is positioned at the other side of said leg 48. A hole (not indicated) extends through the respective side connectors 68 and 70 so that the hole in one side connector 68 will align with the hole in a adjacent side connector 70, when all the legs are assembled in position as shown in FIG. 7. Screws (not indicated) are inserted from the bottom side of the central body 62 into the aligned holes to engage with inner threads defined in the hole of the side connector 70 (the connector in the higher position), thereby securing the side connectors of adjacent legs 48 together.

The central body 62 formed with the sectorial fraction 62a in the shell configuration, substantially houses the side connectors 68, 70 of the respective legs 48 when assembled so that the side connectors 68, 70 are not visible from a top view of the I.V. stand 20. The side connectors 68, 70 are also not visible from a bottom view of the I.V. stand when the plate 67 is attached to the bottom side of the central body 62.

It should be noted that the substantially sectorial side connector 68 may further have an enlarged tip portion 72 (see FIG. 7) which is configured to function as a positioning element to provide convenience of angularly positioning the legs 48 for the assembly procedure and to substantially define a bottom opening of the central passage 46. A top opening of the central passage 64 is also defined by the shell configuration of the sectorial fractions 62a in combination, when the legs 48 are assembled together. The top and bottom openings of the central passage 64 of the central body 62 have an inner diameter slightly greater than the outer diameter of the bottom section 30 of the pole 22 in order to ensure an appropriate fit when the bottom section 30 of the pole 22 is inserted into the base assembly 24. The center wall 66 in the shell configuration of the respective sectorial fractions 62a is configured to not interfere with the insertion of the bottom end 30 of the pole 22, as more clearly shown in FIG. 4. Optionally, the bottom opening of the central passage 46 formed by the enlarged tip portions 72 of the sectorial side connectors 68, may have a diameter smaller than the outer diameter of the bottom section 30 of the pole 22 to prevent the pole 22 from being over-inserted into the base assembly 24, but allowing the fastener to pass therethrough to secure the pole 22 to the base assembly 24.

Each leg 48 may be of an integral two-piece configuration having a first material containing a core element of a second material which is heavier and stronger than the first material. According to one embodiment as shown in FIG. 4, the leg 48 may include a steel band 74 bent in a configuration desirable for the leg 48, as shown in FIG. 5. An outer layer composed of a second material, for example an aluminium alloy outer layer 76, is formed in a molding process to completely surround the steel band 74 in order to form the desired leg configuration. This integral two-piece configuration advantageously provides all the advantages of an aluminium alloy to a base of an I.V stand including an aesthetically pleasing appearance, convenience of manufacturing, resistance to rust etc., while overcoming the disadvantage of lacking stability because the aluminium alloy is relatively light and unable to sustain heavy loads in comparison with steel.

Figure 9:
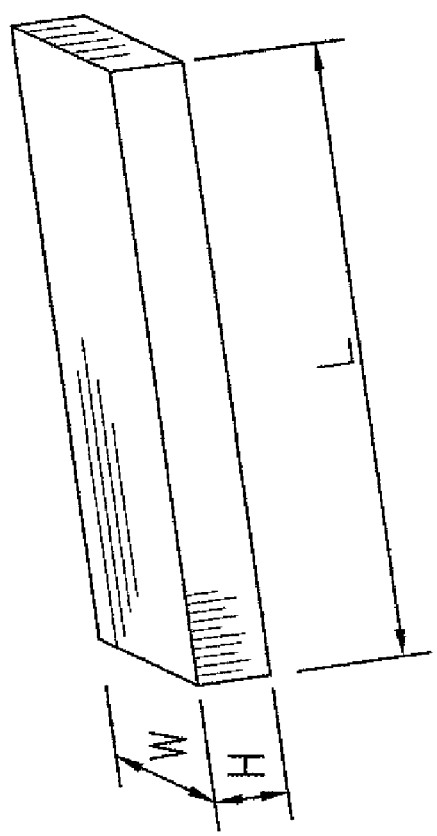
FIG. 9 is a schematic illustration of a box for containing a package of a kit to be assembled into the intravenous stand of FIG. 1.
Figure 8:
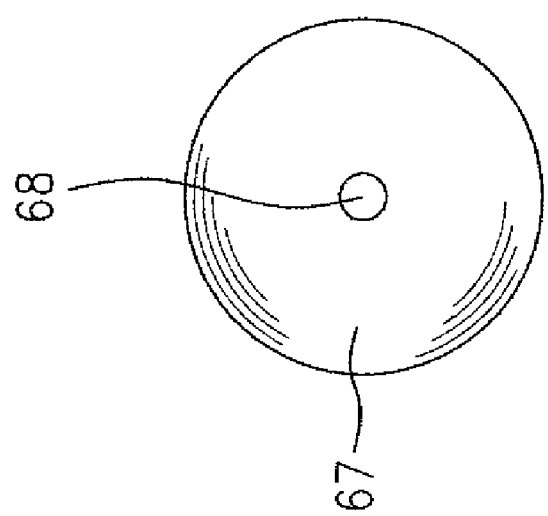
FIG. 8 is a top plane view of a bottom plate used to cover the side connectors of the connected legs from a bottom side.

The further advantage of the I.V. stand according to the embodiments of this invention, lies in that the I.V. stand 20 can be completely disassembled and packaged into a relatively compact kit of components as described above, in contrast to the package size for conventional I.V. stand assemblies. Hospitals often purchase and store large quantities of I.V. stand assemblies. The problem with conventional products is that the pole cannot be collapsed to less than a length of 4.5 feet and the base which is typically manufactured as a complete unit cannot be disassembled and is therefore bulky and unwieldy. The larger size of the packages for such conventional I.V. stands adds to the cost of shipping and requires larger storage space and as such poses a significant problem. The I.V. stand 20 can be provided in a kit package contained in a rectangular box as shown in FIG. 9, having the smaller and more compact dimensions L×W×H wherein L is between 34.5 inches and 34 inches, W is between 6 inches and 5.5 inches and H is between 5 inches and 4.5 inches, which reduces shipping costs and takes up much less storage space.

The above description is meant to be exemplary only and one skilled in the art will recognize that changes may be made to the embodiments described without departure from the scope of the invention disclosed. For example, the core element and the surrounding outer layer of the legs may be made with materials other than steel and aluminium alloy, such as iron and plastic, etc. The connectors of the respective legs may be configured differently from the above-described configurations to similarly achieve a direct connection of adjacent legs without a separate connector, as the described embodiment does. Still other modifications which fall within the scope of the present invention will be apparent to those skilled in the art in light of a review of this disclosure and such modifications are intended to fall within the appended claims.

We claim:

1. An intravenous support apparatus comprising:
    a pole;
    means attachable to the pole for hanging an intravenous liquid supply on the pole;
    a base including a plurality of disconnectable legs having respective inner ends, each inner end being integrated with a sectorial fraction of a central body of the base, the sectorial fractions disassemble-ably joined one with another to form said central body of the base to define a central passage extending vertically through the base, the central passage receiving a bottom end of the pole for supporting the pole in a upright position, the sectorial fractions each being of a shell-configuration and projecting upwardly from the inner end of the respective legs, thereby in combination forming a hollow configuration defined by a peripheral shell wall to present an upwardly projecting profile of the central body of the base in order to provide a vertical dimension for securing the bottom end of the, pole; and
    wherein each of the legs comprises a first material surrounding a core element comprising a second material and wherein the sectorial fractions of the central body comprise the first material only, the first material of the sectorial fractions and the legs being integrated together, respectively.

2. The intravenous support apparatus as defined in claim 1 wherein the base comprises a plurality of wheels each attached to an outer end of the respective legs.

3. The intravenous support apparatus as defined in claim 2 wherein the legs are bent such that the central body formed with the inner ends of the respective legs is positioned lower than the outer ends of the respective legs.

4. The intravenous support apparatus as defined in claim 1 wherein the legs are substantially identical, the inner end of the respective legs being integrated with a pair of side connectors, the side connectors of adjacent legs being connected one to another in order to join the inner ends of the legs together.

5. The intravenous support apparatus as defined in claim 1 wherein the first material of the leg is aluminum.

6. The intravenous support apparatus as defined in claim 1 wherein the second material of the core element of the leg is steel.

7. The intravenous support apparatus as defined in claim 1 wherein each of the legs comprises a steel band as the core element surrounded by molded aluminum.

8. The intravenous support apparatus as defined in claim 1 wherein the pole comprises a top section having an outer diameter and a bottom section having an inner diameter greater than the outer diameter of the top section, the top section being adjustably connected to the bottom section in a telescoping configuration.

9. The intravenous support apparatus as defined in claim 8 wherein the bottom section of the pole comprises an upper part and a lower part, both having the inner diameter of the bottom section, the upper and lower parts being disconnectable one from another.

10. The intravenous support apparatus as defined in claim 9 wherein the upper and lower parts of the bottom section of the pole are tubular to allow a joint member to join the upper and lower parts together by insertion into an inside of both the upper and lower parts.

11. A kit for an assembly of an intravenous support apparatus, the kit comprising:
a first section of a pole;
a hollow second section of the pole for receiving the first section in a telescoping configuration;
a hollow third section of the pole;
a joint element for joining the second and third sections together;
means attachable to the pole for hanging an intravenous liquid supply on the pole; and
a plurality of legs to be joined to form a base for supporting the pole in an upright position, the legs having respective inner ends, each inner end being integrated with a sectorial fraction of a central body of the base, the sectorial fractions being adapted for disassemble-ably joining one with another to form the central body defining a central passage for receiving a bottom end of the pole, the sectorial fractions each being of a shell-configuration and projecting upwardly from the inner end of the respective legs, thereby in combination forming a hollow configuration defined by a peripheral shell wall to present an upwardly projecting profile of the central body of the base in order to provide a vertical dimension for securing the bottom end of the pole and wherein each of the legs comprises a first material surrounding a core element comprising a second material and wherein the sectorial fractions of the central body comprise the first material only, the first material of the sectorial fractions and the legs being integrated together, respectively.

12. The kit as defined in claim 11 further comprising a plurality of wheels to be attached to outer ends of the respective legs.

13. The kit as defined in claim 11 wherein the second and third sections of the pole have an substantially equal inner diameter greater than an outer diameter of the first section of the pole.

14. The kit as defined in claim 11 wherein the legs are substantially identical, the inner end of the respective legs being integrated with a pair of side connectors, the side connectors of the respective legs being adapted to be positioned adjacent one another and to be connected, thereby joining the inner ends of the legs together.

15. The kit as defined in claim 14 wherein the inner end of the respective legs is integrated with a sectorial fraction of the central body of the base, the sectorial fraction of each leg projecting upwardly from the inner end of the leg.

16. The kit as defined in claim 11 wherein the all components of the kit are configured and sized to allow being packed within a package size not greater than 34.5 inches ×6 inches ×5 inches.

* * * * *